United States Patent [19]

Hirata et al.

[11] 4,379,158

[45] Apr. 5, 1983

[54] ANTISECRETORY IMIDAZOLE AMIDINE COMPOUNDS, COMPOSITION AND METHOD OF USE

[75] Inventors: Yasufumi Hirata, Omiya; Isao Yanagisawa; Toshinari Tamura, both of Tokyo; Masaaki Takeda, Urawa, all of Japan

[73] Assignee: Yamanouchi Pharmaceutical Co., Ltd., Tokyo, Japan

[21] Appl. No.: 193,742

[22] Filed: Oct. 3, 1980

Related U.S. Application Data

[63] Continuation-in-part of Ser. No. 934,276, Aug. 16, 1978, Pat. No. 4,252,819.

[30] Foreign Application Priority Data

Aug. 29, 1977 [JP] Japan .............................. 52-104079
Jul. 17, 1978 [JP] Japan .............................. 53-86944

[51] Int. Cl.³ ............... A61K 31/615; C07D 233/64; A61K 31/444; C07D 401/12

[52] U.S. Cl. .............................. 424/273 R; 548/342; 546/210; 546/278; 544/139; 424/263; 424/267; 424/248.4; 424/248.5; 424/248.52; 424/248.53; 424/248.56

[58] Field of Search ............... 548/342; 424/273 R, 424/267, 248.4, 248.5, 248.52, 248.53, 248.56, 424/263; 544/139; 546/210, 278

[56] References Cited

U.S. PATENT DOCUMENTS

3,558,640 1/1971 Shen et al. .......................... 548/342
4,104,382 8/1978 Black et al. ..................... 424/273 R

FOREIGN PATENT DOCUMENTS

1398426 6/1975 United Kingdom .

Primary Examiner—Henry R. Jiles

Attorney, Agent, or Firm—Burgess, Ryan and Wayne

[57] ABSTRACT

Novel heterocyclic compounds shown by the formula

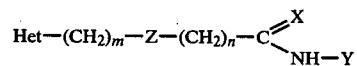

wherein Het represents a 5-membered or 6-membered heterocyclic group which may have substituent(s); Z represents a sulfur atom or oxygen atom; X represents an oxygen atom or the unsubstituted or substituted imino group shown by N—$R_1$ (wherein $R_1$ is a hydrogen atom, a lower alkyl group, a cyano group, an unsubstituted or alkyl substituted carbamoyl group, an unsubstituted or lower alkyl substituted thiocarbamoyl group, or a lower alkanoylamino group); Y represents a hydrogen atom, a lower alkyl group which may have substituent(s), a cycloalkyl group of 3-6 carbon atoms, a lower alkenyl group, a lower alkynyl group, an aryl group which may have substituent(s), an aralkyl group which may have substituent(s), a hydroxyl group, a cyano group, a carbamoyl group, an amidino group, an alkanoyl group which may have been substituted by halogen atom(s), an alkanoylamino group, an arylcarbonylamino group, an alkylamino group, an arylamino group, an arylsulfamoyl group, a lower alkoxycarbamoyl group, or an oxamoylamino group; and m and n represent an integer of 1-3; when X is N—$R_1$, said X and Y may combine with each other to form a 5-membered or 6-membered heterocyclic ring containing 2-3 nitrogen atoms which may have substituent(s), and the pharmacologically acceptable acid addition salts thereof.

The compounds of this invention are useful as gastric acid secretion inhibitors.

9 Claims, No Drawings

ANTISECRETORY IMIDAZOLE AMIDINE COMPOUNDS, COMPOSITION AND METHOD OF USE

CROSS-REFERENCE TO RELATED APPLICATION

This application is a continuation-in-part of copending U.S. application Ser. No. 934,276, filed Aug. 16, 1978, now U.S. Pat. No. 4,252,819.

DETAILED DESCRIPTION OF THE INVENTION

The present invention relates to novel heterocyclic compounds useful as gastric acid secretion inhibitors, the processes of producing them, and the medical compositions containing them.

Thus, according to this invention, there are provided novel heterocyclic compounds represented by the general formula I

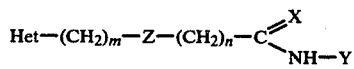   I wherein Het represents a 5-membered or 6-membered heterocyclic group which may have substituent(s); Z represents a sulfur atom or an oxygen atom; X represents an oxygen atom or the unsubstituted or substituted group shown by the formula N—$R_1$ (wherein $R_1$ represents a hydrogen atom, a lower alkyl group, a cyano group, an unsubstituted or lower alkyl-substituted carbamoyl group, an unsubstituted or lower alkyl-substituted thiocarbamoyl group, or a lower alkanoylamino group); Y represents a hydrogen atom, a lower alkyl group which may have substituent(s), a cycloalkyl group of 3–6 carbon atoms, a lower alkenyl group, a lower alkynyl group, an aryl group which may have substituent(s), an aralkyl group which may have substituent(s), a hydroxyl group, a cyano group, a carbamoyl group, an amidino group, an alkanoyl group which is substitutable by halogen atom(s), an alkanoylamino group, an arylcarbonylamino group, an alkylamino group, an arylamino group, an arylsulfamoyl group, a lower alkoxycarbamoyl group, or an oxamoylamino group; and m and n each represents an integer of 1–3; when X is N—$R_1$, said X and Y may combine with each other to form a 5-membered or 6-membered heterocyclic ring containing 2–3 nitrogen atoms which may have substituent(s), and the acid addition salts of the heterocyclic compounds capable being supplied for medical purposes.

Furthermore, according to other embodiments of this invention, there are provided a process of producing the novel heterocyclic compounds of general formula I and the medical compositions containing the novel heterocyclic compounds.

Now, in general formula I shown above, Het is a 5-membered or 6-membered heterocyclic group which may have substituent(s) and practical examples of such a heterocyclic group are isothiazolyl group, imidazolyl group, pyrazolyl group, thiazolyl group, pyrrolyl group, pyridazinyl group, pyrimidinyl group, pyrazinyl group, pyridyl group, triazolyl group, furyl group, and thienyl group. Also, the heterocyclic group may have substituent(s) and examples of such a substituent are, for example, a halogen atom, hydroxyl group, lower alkyl group, lower alkoxy group, hydroxymethyl group, phenyl group, benzyl group, cyano group, amino group, aminoalkyl group, amidino alkyl group, etc. Also, the term "lower" in the explanation of the aforesaid general formula means a straight or branched carbon chain having 1–5 carbon atoms. Therefore, as a lower alkyl group, there are the methyl group, ethyl group, isopropyl group, butyl group, etc.; as a lower alkenyl group, there are the vinyl group, allyl group, isopropenyl group, etc.; as a lower alkynyl group, there are the ethynyl group, 2-propynyl group, 4-pentynyl group, etc.; and as a lower alkanoylamino group, there are the acetylamino group, propionylamino group, isobutyrylamino group, etc. Also, as the aralkyl group, there are the benzyl group, pyridylmethyl group, etc. Moreover, these lower alkyl groups, aryl groups, and aralkyl groups may have substituent(s) such as, for example, the hydroxyl group, amino group, halogen atom, etc.

Then, X and Y in the general formula may combine with each other to form a heterocyclic group such as, for example, 1,2,4-oxadiazol-3-yl group, 1,2,4-triazol-3-yl group, 1,3,5-triazine-2-yl group, pyrimidine-2-yl group, dihydropyridine-2-yl group, tetrahydropyrimidine-2-yl group, imidazol-2-yl group, etc., and these heterocyclic rings may further have substituent(s) such as, for example, the amino group, hydroxyl group, oxo group, lower alkyl group, halogen atom, lower alkoxycarbonyl group, carbamoyl group, etc.

Furthermore, the compounds of the aforesaid general formula I easily form acid addition salts thereof and there also exist the tautomers of these compounds. Therefore, the invention includes also these acid addition salts and the tautomers of the heterocyclic compounds of general formula I.

As mentioned above, the heterocyclic compounds of this invention readily form acid addition salts capable of being used for medical purposes. As these salts, there are the salts of the heterocyclic compounds with inorganic acids and organic acids. Examples of the inorganic acid salts are, for example, hydrochlorides, hydrobromides, and sulfates. Also, examples of the particularly useful organic acid salts are the salts with aliphatic carboxylic acids such as acetic acid, maleic acid, and fumaric acid.

It is the first feature of this invention that the compounds provided by this invention as characterized by a gastric acid inhibitory activity and this activity is not caused by an anticholinergic activity. Since conventional commercially available gastric acid secretion inhibitors are mostly based on the anticholinergic activity and unwanted side effects caused by the anticholinergic activity have been pointed out, the compounds of this invention are useful as new type gastric acid secretion inhibitors.

It is the second feature of this invention that some of the compounds of this invention have an activity for inhibiting gastric acid secretion through a histamine $H_2$-receptor.

It has been proposed to classify histamine receptors into $H_1$-receptors and non $H_1$-receptors or $H_2$-receptors by Ash and Schild; "Brit. J. of Pharmacol. Chemother", 27, 427(1966) and Black et al.; "Nature", 236, 385(1972). The effects of histamine on gastric acid secretion and heart rate in the Guinea pig isolated atrium is mediated by the $H_2$-receptor and these effects are not inhibited by conventional antihistamines such as mepyramine but are antagonized by blockers of $H_2$-receptors such as metiamide.

Since a histamine $H_2$-receptor blocking agent inhibits the basic secretion of gastric acid and the gastric acid secretion induced by gastrin or by food, it can be used for the treatment of gastric ulcer and duodenal ulcer caused by the hypersecretion of gastric acid.

Although the materials possessing the features as in the compounds of this invention, 2-phenyl-2-(2-pyridyl)-thioacetamide (Cook & Bianchi; "Life Sci."; 6, 1381(1967)) the compounds in Belgian Pat. Nos. 779,775; 804,145; 857,388; etc., are known, the compounds of this invention however are all novel compounds having different structures from the known compounds.

The compounds of this invention can be administered orally or parenterally but the oral administration is preferred. The compounds of this invention are used as the free bases or the pharmacologically acceptable salts thereof and, in general, they are used as medical or pharmaceutical compositions with carriers or diluents which can be used generally for preparing medicaments. In the case of oral administration, it is most convenient to use the medical compositions of this invention in the form of capsules or tablets but they may be used as suspended release preparations. Furthermore, the compositions may be used as sugar-coated preparations or syrups. The doses thereof at oral administration are 0.4 to 1 g. per day and it is proper to administer the medicament in 1 to 4 divided doses.

The compounds of this invention shown by general formula I are inhibitors for gastric acid secretion induced by histamine, which will be proved by the following tests:

(i) Effect of test compounds on gastric acid secretion in pylorus-ligated rats

Rats weighing about 200 g. were deprived of food for 24 hours and their pylorus was ligated after an abdominal incision under ether anesthesia (Shay, H. et al.: Gastroenterol., 5, 43, 1945). Test compounds were intraduodenally given immediately after the pylorus ligation. The animals were sacrificed 4 hours after drug administration and gastric contents were collected. The gastric juice was titrated with 0.05 N NaOH to pH 7.0 for measurement of acidity.

As shown in table 1, the compounds reduced significantly the volume of gastric juice and acid secretion.

TABLE 1

| | Effect of test compounds on gastric acid secretion in pylorus-ligated rats | | | |
|---|---|---|---|---|
| | Dose | | Gastric contents | |
| Compound | mg/kg; id | No. of animals | Volume ml/4 hours/rat | Acid output μEq/4 hours/rat |
| Control | — | 7 | 3.2 ± 0.3 | 380 ± 40.1 |
| Example 44 | 50 | 7 | 1.4 ± 0.2* | 79 ± 9.0* |
| Example 41 | 50 | 7 | 1.5 ± 0.2* | 97 ± 17.2* |
| Example 42 | 50 | 7 | 1.7 ± 0.3* | 137 ± 31.5* | id: intraduodenal administration,
Values represent mean ± S.E.
*: $p < 0.01$ (ii) Histamine $H_2$-receptor blocking activity of test compounds in isolated guinea-pig atria Atrial preparations isolated from guinea-pigs were suspended in Krebs-Henseleit solution at 36° C. (Mitchell, I. et al. Europ. J. Pharmacol., 34, 95, 1975). The dose producing a 50% blockade of chronotropic action of $5 \times 10^{-6}$ M histamine was obtained from the doserespose curve in which the inhibition percentage was plotted semilogarithmically against dose.

As shown in Table 2, the compounds inhibited histamine-induced tachycardia in isolated atrial preparations.

TABLE 2

| Antagonistic activity of test compounds on histamine-induced tachycardia in isolated atria of guinea-pigs | |
|---|---|
| Compound | $ED_{50}$, M |
| Example 44 | $(0.9 \pm 0.1) \times 10^{-6}$ |
| Example 40 | $(2.3 \pm 0.4) \times 10^{-6}$ |
| Example 41 | $(2.1 \pm 0.2) \times 10^{-6}$ |

Values represent mean ± S.E. from 5 experiments.

The heterocyclic compounds of this invention shown by general formula I can be produced by the following process:

Production process 1

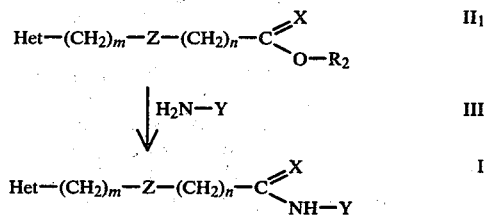

in the formulae, $R_2$ represents a lower alkyl group and Het, X, Y, Z, m and n have the same significance as above.

This process is performed by reacting the starting compound of formula $II_1$ and a reactive amount of the amine of formula III. Examples of the amine shown by formula III used in the process are, for example, ammonia; a lower alkylamine such as methylamine, ethylamine, trifluoroethylamine, etc.; a cycloalkylamine such as cyclopropylamine, etc.; a lower alkenylamine such as allylamine, etc.; a lower alkynylamine such as 2-propynylamine, etc,; an aralkylamine such as benzylamine, pyridylmethylamine, etc.; an aromatic amine such as aniline, etc,; a hydrazine such as hydrazine, acetylhydrazine, benzoylhydrazine, α-picolinylhydrazine, benzenesulfonylhydrazine, oxamoylhydrazine, alkyl-, aryl- or aralkyl-substituted hydrazine, etc.; an amidine such as formamidine, acetamidine, propionamidine, etc.; glycine, β-alanine or the esters of them; aminomalonic acid diester, aminoacetaldehyde diacetal, etc,; 3-aminoacrylic acid ester; urea; guanidine; cyanamide; and the like.

The reaction is usually performed in a solvent and suitable solvents, include alcohol, isopropanol, chloroform, ether, tetrahydrofuran, benzene, etc. It is preferred that these solvents do not contain water. There is no particular restriction about the reaction temperature but the reaction is preferably performed at room temperature or under heating. Also, it is preferred that the reaction system is in a neutral to basic state.

In the reaction, depending on the group or element represented by X in the starting compound of formula $II_1$ and the kind of the amine of formula III to be reacted therewith, X and Y of the heterocyclic compound of formula I may, as the case may be, combine with each other to form a 5-membered or 6-membered ring in the objective compound. For example, there are the case of reacting the compound of formula $II_1$ wherein X is an imino group (=NH) and a hydrazine compound such as acetylhydrazine, benzoylhydrazine, etc.; aminomalonic acid diester; glycine ester; aminoacetaldehyde dialkylacetal (e.g., $H_2NCH_2CH(OC_2H_5)_2$); 3-acrylic acid ester (e.g., $H_2N-CH=CHCOOC_2H_3$) etc., the case of reacting the compound of formula $II_1$ wherein X is a cyanoimino group (=N—CN) and a hydrazine, a hydroxylamine, or an amidine, and the case of reacting the compound of formula $II_1$ wherein X is a lower alcanoylaimino group (=N—CO-lower alkyl) and an amidine.

In these cases, the cyclized desired product of this invention may be obtained directly by the reaction of the raw material compound of formula $II_1$ and the amine of formula III but the cyclized objective compound of this invention may be prepared stepwise by forming once the uncyclized desired product of this invention shown by formula I and then continuing the reaction in situ or by changing the reaction conditions.

Production Process 2

$$Het-(CH_2)_m-Z-(CH_2)_n-COOH \quad II_2$$

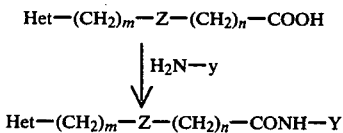

$$Het-(CH_2)_m-Z-(CH_2)_n-CONH-Y \quad I_2$$

in the formulae, Het, Y, Z, m and n have the same significance as above.

In the process, the desired product of this invention is prepared by the synthesis of an ordinary acid amide. As a particularly preferred process, there is an acid chloride process, another process wherein a condensing agent such as dicyclohexylcarbodiimide is used, and an alternative process wherein an active ester such as chlorocarbonic acid ester is used. The synthesis of the acid amide is usually performed in an inert solvent such as, preferably, chloroform, ether, tetrahydrofuran, benzene, etc. Also, there is no particular restriction about the reaction temperature but it is preferred to perform the reaction at room temperature or under heating.

Other Production Processes

The desired product of formula $I_2$ in Production process 2 wherein n is 2 and Y is hydrogen atom, a lower alkyl group, an aryl group, or an aralkyl group can be also obtained by reacting the alcohol or thiol represented by the general formula $$Het-(CH_2)_m-Z-H \quad II_3$$

wherein Het, Z and n have the same significance as above and acrylic amide or a derivative thereof under heating in the presence of a base such as sodium alkoxide.

Furthermore, as an alternative process of producing the desired products of this invention, there is a process of converting mutually $R_1$ of the desired product of formula I wherein X is =N—$R_1$. For example, there are the following processes:

(i) The desired product of formula I wherein $R_1$ is a cyano group is obtained by reacting the hydrochloride of the corresponding compound of formula I wherein $R_1$ is hydrogen atom and the monosodium salt of cyanamide.

(ii) The desired product of formula I wherein $R_1$ is a carbamoyl group or a thiocarbamoyl group can be prepared as follows:

(a) The compound of formula I wherein $R_1$ is a carbamoyl group is obtained by passing dry hydrogen chloride gas through an alcohol containing the compound of formula I wherein $R_1$ is a cyano group, while cooling or treating said compound with concentrated hydrochloric acid and by further treating the product with phosphorus pentasulfide; the product is converted into a compound of formula I wherein $R_1$ is a thiocarbamoyl group.

(b) The compound of formula I wherein $R_1$ is a carbamoyl group or a thiocarbamoyl group is obtained by reacting the compound of formula I wherein $R_1$ is hydrogen atom and an isocyanic acid derivative such as methyl isocyanate or an isothiocyanic acid derivative such as methylisocyanate.

(iii) The desired product of formula I wherein X and Y combine with each other to form a pyrimidine-2-yl group or a dihydropyrimidine-2-yl group is obtained by reacting a compound of formula I whether $R_1$ is hydrogen atom and Y is a hydrogen atom or a lower alkyl group and cyanoacetic acid ethyl ester, malonic acid diethyl ester, acetoacetic acid ethyl ester, etc.

(iv) The compound of formula I wherein X is an imino group (=NH) and Y is a halogen-substituted alkanoyl group is obtained by reacting the compound shown by the formula

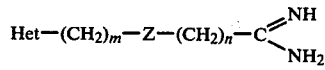

wherein Het, Z, m and n have the same significance as above and a halogenoacetic acid ester.

Then, the process of this invention will further be explained by the following examples. In addition, the starting compounds used in the process of this invention can be prepared according to the processes shown in the following reaction formulae, the details of which will be described in the examples.

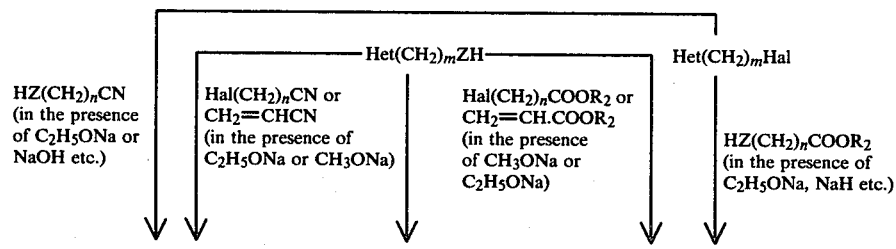

-continued

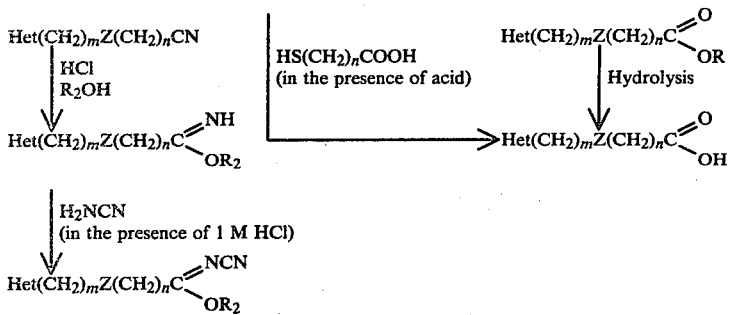

(In the formulae, Hal represents halogen atom and Het, Z, R₂, m and n are same as above.)

EXAMPLE 1

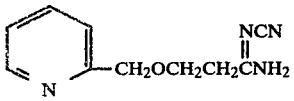

(a) To 28.5 g. of 2-hydroxymethyl pyridine was added 0.3 g. of sodium methoxide and while maintaining the reaction mixture at 40°–50° C. with ice-cold water, 14 g. of acrylonitrile was added dropwise to the mixture gradually with stirring. Thereafter, the reaction mixture was stirred for one hour at 50° C. and after adding thereto 0.33 g. of acetic acid, the mixture was distilled under reduced pressure to provide 38.9 g. of oily 3-(2-pyridylmethoxy)propionitrile. Boiling point: 102°–104° C. (0.2 mm. Hg).

(b) In 14.2 g. of absolute ethanol was dissolved 10 g. 3-(2-pyridylmethoxy)propionitrile and while cooling the solution to 0°–5° C., 5 g. of a dry hydrogen chloride gas was added into the solution. The solution was allowed to stand for one week in a refrigerator. Then, 30 ml. of dry ether was added to the solution and 15.0 g. of the crystals of ethyl 3-(2-pyridylmethoxy)propionimidate dihydrochloride were recovered by filtration. The crystals were dissolved in 30 ml. of ice water, after being alkalified with potassium carbonate, the solution was extracted three times each time with 40 ml. of ether, and the ether layers were dried over potassium carbonate. Then, the solvent was distilled off under reduced pressure to provide 10.8 g. of ethyl 3-(2-pyridylmethoxy)propionimidate.

(c) In 3 ml. of dry ethanol was dissolved 5.0 g. of ethyl 3-(2-pyridylmethoxy)propionimidate and then 1.1 g. of cyanamide was added to the solution. After allowing to stand the mixture for 30 minutes at room temperature, the solvent was distilled off under reduced pressure and the residue was purified by means of silica gel column chromatography using methylene chloride-ethyl acetate as an eluent and recrystallized from ethyl acetate-ether to provide 1.2 g. of N-cyano-3-(2-pyridylmethoxy)propionamidine showing a melting point of 87°–89° C.

| Elemental analysis for C₁₀H₁₂N₄O: | | | |
|---|---|---|---|
| | C | H | N |
| Calculated: | 58.81% | 5.92% | 27.43% |
| Found: | 58.13% | 5.93% | 27.83% |

EXAMPLE 2

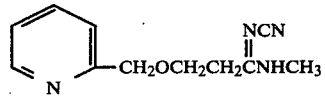

In 30 ml. of dry ethanol was dissolved 7 g. of ethyl 3-(2-pyridylmethoxy)propionimidate dihydrochloride and after cooling the solution to 0°–5° C. with ice-cold water, 2.5 g. of triethylamine and then 1.0 g. of cyanamide were added to the solution followed by stirring for 3 hours at room temperature. Then, the solvent was distilled off under reduced pressure and the residue formed was mixed with 30 ml. of water and extracted three times each time with 40 ml. of methylene chloride. The methylene chloride layer was washed with water, dried over anhydrous magnesium sulfate, and concentrated under reduced pressure to provide 4.0 g. of ethyl N-cyano-3-(2-pyridylmethoxy)propionimidate. The product was dissolved in 10 ml. of dry methanol and after adding thereto 10 ml. of a 40% methanol solution of methylamine, the mixture was allowed to stand for 30 minutes at room temperature. Then, the reaction mixture was concentrated under reduced pressure and the residue was purified by silica gel column chromatography using a mixed solvent of methylene chloride and ethyl acetate as an eluant to provide 2.0 g. of oily N-cyano-N'-methyl-3-(2-pyridylmethoxy)-propionamidine.

Infrared absorption spectrum (neet): 2170 cm.⁻¹

Nuclear magnetic resonance spctra (CDCl₃). δ: 2.93 (3H, d, J=5 Hz, —NHCH₃); 2.99 (2H, t, J=6 Hz, OCH₂CH₂); 3.85 (2H, t, J=6 Hz, OCH₂CH₂); 4.70 (2H, s, —CH₂O—CH₂O—CH₂CH₂); 7.2~9.2 (5H,

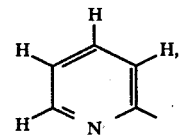

NHCH₃)

Mass spectrum: m/e 218(M+), 188, 163

EXAMPLE 3

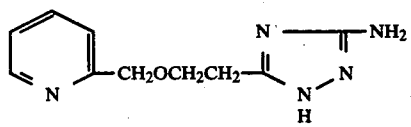

In 30 ml. of dry ethanol was dissolved 5.6 g. of ethyl N-cyano-3-(2-pyridylmethoxy)propionimidate and the solution was added dropwise to a solution of 0.77 g. of hydrazine in 20 ml. of dry ethanol followed by stirring for one hour at room temperature. The solvent was distilled off under reduced pressure and the residue formed was recrystallized from a mixed solvent of ethanol and ether to provide 1.85 g. of the crystals of 3-amino-5[2-(2-pyridyl)methoxy]ethyl-1,2,4-triazole showing a melting point of 124°-125° C.

| Elemental analysis for $C_{10}H_{13}N_5O$: | | | |
|---|---|---|---|
| | C | H | N |
| Calculated: | 54.78% | 5.98% | 31.94% |
| Found: | 54.60% | 6.05% | 31.91% |

EXAMPLE 4

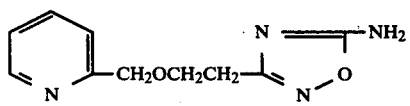

In 30 ml. of dry ethanol was dissolved 2 g. of hydroxylamine hydrochloride and after cooling the solution to 0°-5° C. with ice-cold water, 2.9 g. of triethylamine and then 30 ml. of a dry ethanol solution of 7.0 g. of ethyl N-cyano-3-(2-pyridylmethoxy)propionimidate were added dropwise to the solution. Then, the mixture was allowed to rise to room temperature followed by stirring for one hour. The solvent was distilled off under reduced pressure and the residue formed was purified by means of a silica gel column chromatography using a mixed solvent of methylene chloride and ethyl acetate as an eluant and recrystallized from a mixed solvent of ethyl acetate and n-hexane to provide 1.3 g. of the colorless crystals of 5-amino-3-[2-(2-pyridylmethoxy)ethyl]-1,2,4-oxadiazole showing a melting point of 120°-122° C.

| Elemental analysis for $C_{10}H_{12}N_4O_2$: | | | |
|---|---|---|---|
| | C | H | N |
| Calculated: | 54.54% | 5.49% | 25.44% |
| Found: | 54.37% | 5.37% | 25.22% |

EXAMPLE 5

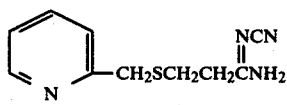

(a) To 13 g. of 2-mercaptomethyl pyridine was added 0.15 g. of sodium methoxide and while maintaining the reaction mixture at 40°-50° C. with ice-cold water, 5.2 g. of acrylnitrile was added dropwise gradually to the mixture with stirring. Thereafter, the reaction mixture was stirred for one hour at 50° C., 0.15 g. of acetic acid was added to the mixture, and the reaction mixture was distilled under reduced pressure to provide 15.1 g. of oily 3-(2-pyridylmethylthio)propionitrile showing a boiling point of 124°-125° C. (0.4 mm.Hg).

(b) In 53.1 g. of dry ethanol was dissolved 41.1 g. of 3-(2-pyridylmethylthio)propionitrile and while cooling the solution to 0°-5° C. with ice-cold water, 18.5 g. of dry hydrogen chloride gas was added to the solution. The reaction mixture was allowed to stand for one week in a refrigerator and the crystals deposited were recovered by filtration to provide 60 g. of ethyl 3-(2-pyridylmethylthio)propionimidate dihydrochloride. The product could be converted into the free imidate as in the case of Example 1-(b).

(c) In 10 ml. of dry ethanol was dissolved 10 g. of ethyl 3-(2-pyridylmethylthio)propionimidate and after adding thereto 1.7 g. of cyanamide, the mixture was allowed to stand for 30 minutes at room temperature. Then, the solvent was distilled off under reduced pressure and the residue was purified by means of a silica gel column chromatography using a mixed solvent of methylene chloride and ethyl acetate as an eluant and recrystallized from a mixed solvent of ethyl acetate and ether to provide 4.5 g. of N-cyano-3-(2-pyridyl)-methylthio propionamidine showing a melting point of 110°-112° C.

| Elemental analysis for $C_{10}H_{12}N_4S$: | | | |
|---|---|---|---|
| | C | H | N |
| Calculated: | 54.52% | 5.49% | 25.43% |
| Found: | 54.48% | 5.38% | 25.06% |

EXAMPLE 6

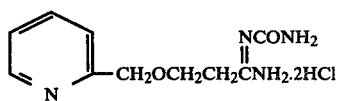

In 15 ml. of dry ethanol was dissolved 1.0 g. of N-cyano-3-(2-pyridylmethoxy)propionamidine and after cooling the solution to 0°-5° C. with ice-water, a dry hydrogen chloride gas was passed through the solution for one hour. Then, the solvent was distilled off under reduced pressure and the residue was recrystallized from a mixed solvent of ethanol and ether to provide 1.55 g. of N-carbamoyl-3-(2-pyridylmethoxy)propionamidine dihydrochloride showing a melting point of 85°-89° C.

| Elemental analysis for $C_{10}H_{16}N_4O_2Cl_2 \cdot \frac{1}{2}H_2O$: | | | |
|---|---|---|---|
| | C | H | N |
| Calculated: | 39.49% | 5.63% | 18.42% |
| Found: | 39.87% | 5.94% | 18.15% |

EXAMPLE 7

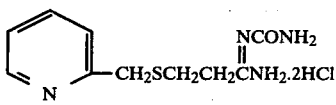

By following the same procedure as in Example 6 using 1.0 g. of N-cyano-3-[(2-pyridyl)methylthio]propionamide, 1.36 g. of N-carbamoyl-3-(2-pyridylmethylthio)propionamide dihydrochloride was obtained.

Melting point: 136°–141° C. (decompd.)

| Elemental analysis for $C_{10}H_{16}N_4OSCl_2$: | | | |
|---|---|---|---|
| | C | H | N |
| Calculated: | 38.59% | 5.18% | 18.00% |
| Found: | 38.48% | 5.32% | 17.25% |

EXAMPLE 8

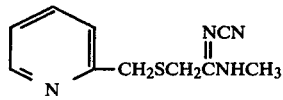

(a) In 150 ml. of dry ethanol was dissolved 2.76 g. of metallic sodium in nitrogen gas stream and then a solution of 15 g. of 2-pyridine thiomethanol in 30 ml. of dry ethanol was added to the solution at room temperature followed by stirring for 2 hours. Then, the mixture was cooled to 0°–5° C. and a solution of 9.06 g. of chloroacetonitrile in 20 ml. of dry ethanol was added dropwise to the mixture followed by stirring for 18 hours at room temperature. Thereafter, the solvent was distilled off under reduced pressure and the residue was dissolved in 50 ml. of water and extracted three times each time with 50 ml. of dichloromethane. The dichloromethane layer was washed with water, dried over anhydrous magnesium sulfate, and concentrated under reduced pressure to provide 21.3 g. of oily 2-pyridylmethylthioacetonitrile.

(b) In 21.5 g. of dry ethanol was dissolved 15.3 g. of 2-pyridylmethylthioacetonitrile and after adding 7.5 g. of a dry hydrogen chloride gas into the solution under cooling to 0°–5° C., the reaction mixture was allowed to stand for one week in a refrigerator. Then, 20 ml. of dry ether was added to the reaction mixture to deposit completely crystals, which were recovered by filtration to provide 24.4 g. of 2-pyridylmethylthioacetimidate dihydrochloride. An aqueous solution of the product was alkalified with potassium carbonate and then extracted with ether to provide the free imidate.

(c) In 30 ml. of dry ethanol was dissolved 10 g. of ethyl 2-pyridylmethylthioacetimidate dihydrochloride and after cooling the solution to 0°–5° C., a solution of 3.5 g. of triethylamine in 10 ml. of dry ethanol was added dropwise to the solution. The mixture was allowed to raise to room temperature and 1.5 g. of cyanamide was added thereto followed by stirring for 3 hours. Then, the solvent was distilled off under reduced pressure and the residue was dissolved in 50 ml. of water and extracted three times each time with 60 ml. of ether. The ether layer was washed with water, dried over anhydrous magnesium sulfate, and concentrated under reduced pressure to provide 7.6 g. of crude ethyl N-cyano-2-pyridylmethylthioacetimidate.

(d) The product obtained in step (c) was dissolved in 10 ml. of methanol and after adding 10 ml. of a methanol solution of 40% methylamine, the mixture was allowed to stand for 15 minutes at room temperature. Then, the reaction mixture was concentrated under reduced pressure and the residue was purified by means of a silica gel column chromatography using a mixed solvent of methylene chloride and ethyl acetate as an eluant and recrystallized from a mixed solvent of ethyl acetate and ether to provide 3.9 g. of the colorless crystals of N-cyano-N'-methyl-2-(2-pyridylmethylthio)acetamidine showing a melting point of 73°–74° C.

| Elemental analysis for $C_{10}H_{12}N_4S$: | | | |
|---|---|---|---|
| | C | H | N |
| Calculated: | 54.52% | 5.49% | 25.43% |
| Found: | 54.54% | 5.45% | 25.76% |

EXAMPLE 9

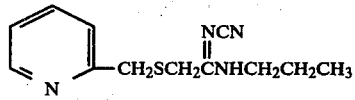

In 20 ml. of dry ethanol was dissolved 2.35 g. of ethyl N-cyano-2-pyridylmethylthioacetimidate obtained as in Example 8 (a), (b) and (c) described above and after adding 5 ml. of dry ethanol solution of 0.59 g. of n-propylamine, the mixture was allowed to stand for 30 minutes at room temperature. Then, the reaction mixture was concentrated under reduced pressure and the residue was purified by means of a silica gel column chromatography using a mixed solvent of methylene chloride and ethyl acetate as an eluant and recrystallized from a mixed solvent of ethyl acetate and n-hexane to provide 1.1 g. of the colorless plates of N-cyano-N'-propyl-2-(2-pyridylmethylthio)acetamidine showing a melting point of 54°–56° C.

| Elemental analysis for $C_{12}H_{16}N_4S$: | | | |
|---|---|---|---|
| | C | H | N |
| Calculated: | 58.04% | 6.49% | 22.56% |
| Found: | 57.95% | 6.53% | 22.77% |

EXAMPLE 10

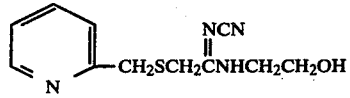

By following the same procedure as in Example 9 using 2.35 g. of ethyl N-cyano-2-pyridylmethylthioacetimidate and 0.61 g. of ethanolamine, 0.75 g. of N-cyano-N'-(2-hydroxyethyl)-2-(2-pyridylmethylthio)acetamidine showing a melting point of 68°–69° C. was obtained.

| Elemental analysis for $C_{11}H_{14}N_4OS$: | | | |
|---|---|---|---|
| | C | H | N |
| Calculated: | 52.78% | 5.64% | 22.38% |
| Found: | 52.82% | 5.58% | 22.57% |

EXAMPLE 11

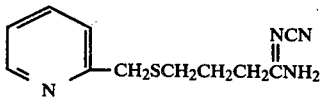

In 40 ml. of dry ethanol was dissolved 21.0 g. of ethyl 4-(2-pyridylmethylthio)butylimidate prepared by following the same procedure as in Example 8 (a) using 4-chlorobutyronitrile in place of chloroacetonitrile and treating the product as in Example 8 (b) and after adding to the solution 4 g. of cyanamide, the mixture was allowed to stand for 30 minutes at room temperature. Then, the reaction mixture was concentrated under reduced pressure and the residue was purified by means of a silica gel column chromatography using a mixed solvent of methylene chloride and ethyl acetate and recrystallized from a mixed solvent of ethanol and ether to provide 9.6 g. of N-cyano-4-(2-pyridylmethylthio)-butyramidine showing a melting point of 96°–97° C.

| Elemental analysis for $C_{11}H_{14}N_4S$: | | | |
|---|---|---|---|
| | C | H | N |
| Calculated: | 56.38% | 6.02% | 23.91% |
| Found: | 55.67% | 6.01% | 23.73% |

EXAMPLE 12

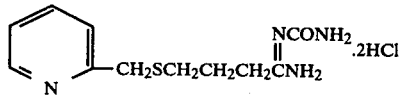

By following the same procedure as in Example 6 using N-cyano-4-(2-pyridylmethylthio)butyramidine, N-carbamoyl-4-(2-pyridylmethylthio)butyramidine dihydrochloride was obtained.

Melting point: 160°–165° C. (decompd.)

| Elemental analysis for $C_{11}H_{18}N_4SCl_2.H_2O$: | |
|---|---|
| | N |
| Calculated: | 17.12% |
| Found: | 16.97% |

EXAMPLE 13

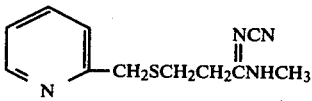

In 80 ml. of dry ethanol was dissolved 15 g. of ethyl 3-(2-pyridylmethylthio)propionimidate dihydrochloride and after cooling the solution to 0°–5° C., 5.1 g. of triethylamine was added to the solution. The mixture was allowed to raise to room temperature and 2.1 g. of cyanamide was added to the mixture followed by stirring for 1.5 hours. The reaction mixture was then concentrated under reduced pressure and the residue was mixed with 50 ml. of water and extracted three times each time with 60 ml. of ether. The ether layer was washed with water and dried over anhydrous magnesium sulfate. Then, the solvent was distilled off under reduced pressure and the residue formed was dissolved in 20 ml. of dry methanol and mixed with 20 ml. of a 40% methanol solution of methylamine. The mixture was allowed to stand for 15 minutes at room temperature and then concentrated under reduced pressure. The residue formed was purified by means of a silica gel column chromatography using a mixed solvent of methylene chloride and ethyl acetate and recrystallized from a mixture of ethyl acetate and ether to provide 2.5 g. of N-cyano-N'-methyl-3-(2-pyridylmethylthio)propionamidine showing a melting point of 49°–51° C.

| Elemental analysis for $C_{11}H_{14}N_4S$: | |
|---|---|
| Calculated: | N 23.91% |
| Found: | N 23.79%. |

EXAMPLE 14

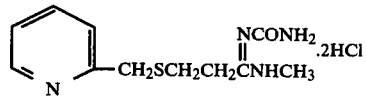

By following the same procedure as in Example 6 using N-cyano-N'-methyl-3-(2-pyridylmethylthio)propionamidine, N-carbamoyl-N'-methyl-3-(2-pyridylmethylthio)propionamidine, dihydrochloride showing a melting point of 155°–160° C. (decompd.) was obtained.

| Elemental analysis for $C_{11}H_{18}N_4SCl_2.2H_2O$ | |
|---|---|
| Calculated: | N 16.23% |
| Found: | N 16.37%. |

EXAMPLE 15

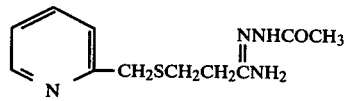

In 50 ml, of dry ethanol was dissolved 7.0 g. of ethyl 3-(2-pyridylmethylthio)propionimidate and a solution of 3.5 g. of acetohydrazide in 20 ml. of dry ethanol was added to the solution with stirring, the reaction was performed for one hour at room temperature.

The solvent was distilled off under reduced pressure and the residue was recrystallized from a mixture of ethanol and ether to provide the colorless crystals of N-acetyl-3-(2-pyridylmethylthio)propionamidrazone showing a melting point of 149°–150.5° C.

EXAMPLE 18

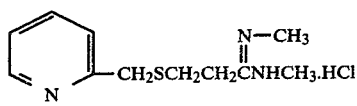

In 20 ml. of a 40% methanol solution of methylamine was dissolved 5.0 g. of ethyl 3-(2-pyridylmethylthio)-propionimidate and after allowing the solution to stand for 20 hours at room temperature, the reaction mixture was concentrated under reduced pressure. Then, the residue formed was purified by means of a silica gel column chromatography using a mixed solvent of methylene chloride and ethyl acetate as an eluant and after adding an equimolar amount of hydrochloric acid, the product was recrystallized from a mixture of ethanol and ether to provide 2.0 g. of N,N'-dimethyl-3-(2-pyridylmethylthio)propionamidine hydrochloride showing a melting point of 142°–143° C.

| Elemental analysis for $C_{11}H_{18}N_3SCl$: | | | | |
|---|---|---|---|---|
| | C | H | N | Cl |
| Calculated: | 50.85% | 6.98% | 16.18% | 13.65% |
| Found: | 51.03% | 6.92% | 16.12% | 13.40% |

EXAMPLE 19

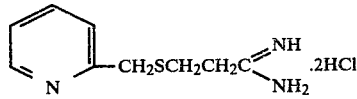

Ethyl 3-(2-pyridylmethylthio)propionimidate was reacted with an equimolar amount of ammonium chloride in methanol for 2 hours at room temperature and the product was recrystallized from a mixture of ethanol and ether to provide 3-(2-pyridylmethylthio)propionamidine dihydrochloride showing a melting point of 140°–143° C.

| Elemental analysis for $C_9H_{15}N_3SCl_2$: | | | |
|---|---|---|---|
| | C | H | N |
| Calculated: | 40.30% | 5.64% | 15.67% |
| Found: | 39.97% | 5.67% | 15.68% |

EXAMPLES 20–33

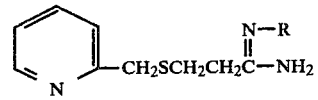

To an absolute ethanol solution of ethyl 3-(2-pyridylmethylthio)propionimidate was added 1.5–5 equivalent of amine (RNH$_2$) and the mixture was allowed to stand for 24 hours at room temperature. Then, the solvent was distilled off under reduced pressure. The crystallized residue was recrystallized from a proper solvent, while the other residue was purified by means of a silica gel column chromatography using a mixed solvent of methylene chloride and methanol and treated with hy-

---

| Elemental analysis for $C_{11}H_{16}N_4OS$: | | | |
|---|---|---|---|
| | C | H | N |
| Calculated: | 52.36% | 6.39% | 22.20% |
| Found: | 52.38% | 6.43% | 22.38% |

EXAMPLE 16

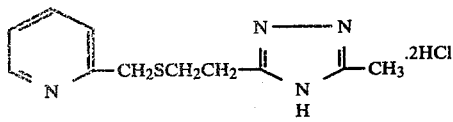

1.7 g. of N-acetyl-3-(2-pyridylmethylthio)-propionamidrazone was heated in an oil bath at 155° C. for 10 minutes, the reaction mixture was allowed to cool to room temperature and dissolved in 20 ml. of dry ethanol. The product was treated with an ethanol solution of hydrogen chloride. Then, the solvent was distilled off under reduced pressure and the residue was recrystallized from a mixture of ethanol and ether to provide 1.7 g. of the colorless crystals of 3-methyl-5-[2-(2-pyridylmethylthio)ethyl]-1,2,4-triazole dihydrochloride showing a melting point of 239°–241° C.

| Elemental analysis for $C_{11}H_{16}N_4SCl_2 \cdot H_2O$: | | | |
|---|---|---|---|
| | C | H | N |
| Calculated: | 40.62% | 5.58% | 17.23% |
| Found: | 41.04% | 5.18% | 17.52% |

EXAMPLE 17

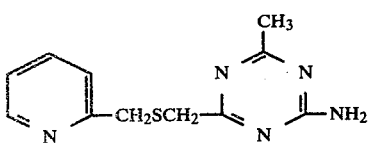

In 20 ml. of dry ethanol was dissolved 5.7 g. of ethyl N-cyano-2-pyridylmethylthioacetimidate and after cooling the solution to 0°–5° C., acetamidine (prepared by liberating 2.3 g. of acetamidine hydrochloride with a solution of 0.57 g. of sodium in 20 ml. of ethanol and filtering off sodium chloride thus formed) was added to the solution. The mixture was allowed to raise to room temperature followed by stirring for one hour and concentrated under reduced pressure. The residue was mixed with 30 ml. of water and extracted three times each time with 40 ml. of methylene chloride. The methylene chloride layer was washed with water, dried over anhydrous magnesium sulfate, and concentrated under reduced pressure. The residue was recrystallized from ethyl acetate to provide 1.6 g. of the colorless crystals of 2-amino-4-methyl-6-(2-pyridylmethylthio)methyl-1,3,5-triazine showing a melting point of 99.5°–101° C.

| Elemental analysis for $C_{11}H_{13}N_5S$: | | | |
|---|---|---|---|
| | C | H | N |
| Calculated: | 53.42% | 5.30% | 28.32% |
| Found: | 53.26% | 5.10% | 28.39% | drochloric acid to provide a hydrochloride, which was recrystallized. By the procedures described above, the following products were obtained.

EXAMPLE 20

Desired Compound

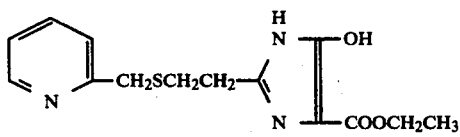

4(5)-Ethoxycarbonyl-5(4)-hydroxy-2-[2-(2-pyridyl-methylthio)ethyl]imidazole
Reagent amine

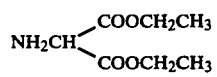

Recrystallization solvent
Ethanol-Ether
melting point
185–187° C.

Elemental analysis for $C_{14}H_{17}N_3O_3S$

|  | C | H | N |
|---|---|---|---|
| Calculated: | 57.41% | 5.57% | 13.67% |
| Found: | 57.80% | 5.60% | 13.70% |

EXAMPLE 21

Desired Compound

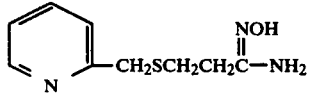

3-(2-Pyridylmethylthio)propionamide oxime (Oily)

Reagent amine: $NH_2OH$.
Nuclear magnetic resonance spectra ($CDCl_3$). δ: 2.38 (2H, t), 2.70 (2H,t), 3.86 (2H,s), 7.0–8.6 (4H).
Mass spectrum: (Trimethylsilylated) m/e 355, 340

EXAMPLE 22

Desired Compound

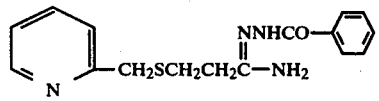

N—Benzoyl-3-(2-pyridylmethylthio)propionamidrazone
Reagent amine

Recrystallization solvent
Ethanol-Ether
melting point
138–139° C.

Elemental analysis for $C_{16}H_{18}N_4OS$

|  | C | H | N |
|---|---|---|---|
| Calculated: | 61.12% | 5.77% | 17.82% |
| Found: | 61.05% | 5.76% | 18.15% |

EXAMPLE 23

Desired Compound

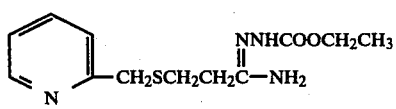

N—Ethoxycarbonyl-3-(2-pyridylmethylthio)propionamidrazone
Reagent amine
$NH_2NHCOOCH_2CH_3$
Recrystallization solvent
Methanol-Ether
melting point
129.5–131° C.

Elemental analysis for $C_{12}H_{18}N_4O_2S$

|  | C | H | N |
|---|---|---|---|
| Calculated: | 51.05% | 6.43% | 19.84% |
| Found: | 50.84% | 6.34% | 19.82% |

EXAMPLE 24

Desired Compound

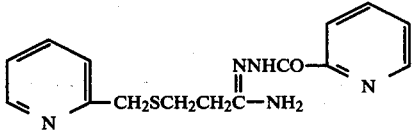

N—[(2-Pyridyl)carbonyl]-3-(2-pyridylmethylthio)-propionamidrazone
Reagent amine

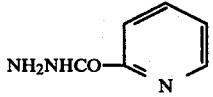

Recrystallization solvent
Ethanol-n-Hexane
melting point
127–129° C.

Elemental analysis for $C_{15}H_{17}N_5OS$

|  | C | H | N |
|---|---|---|---|
| Calculated: | 57.12% | 5.43% | 22.21% |
| Found: | 57.08% | 5.44% | 22.56% |

EXAMPLE 25

Desired Compound

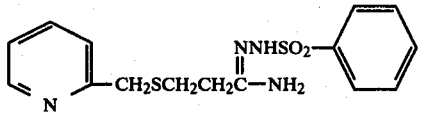

N—Benzenesulfonyl-3-(2-pyridylmethylthio)-propionamidrazone
Reagent amine

-continued

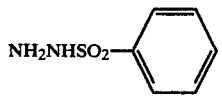

Recrystallization
Aceton-n-Hexane
melting point
119–121° C.

Elemental analysis for $C_{15}H_{18}N_4O_2S_2$

| | C | H | N |
|---|---|---|---|
| Calculated: | 51.41% | 5.18% | 15.99% |
| Found: | 51.20% | 5.12% | 15.93% |

EXAMPLE 26

Desired Compound

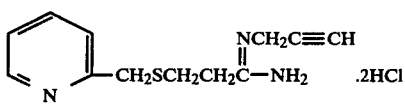

N—(2-Propynyl)-3-(2-pyridylmethylthio)propion-
amidine dihydrochloride
Reagent amine
$NH_2CH_2C\equiv CH$
Recrystallization solvent
Ethanol-Ether
melting point
159–161° C.

Elemental analysis for $C_{12}H_{17}N_3SCl_2$

| | C | H | N |
|---|---|---|---|
| Calculated: | 47.06% | 5.59% | 13.72% |
| Found: | 46.78% | 5.63% | 13.68% |

EXAMPLE 27

Desired Compound

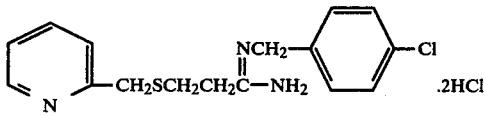

N—(4-Chlorobenzyl)-3-(2-pyridylmethylthio)-
propionamidine dihydrochloride
Reagent amine

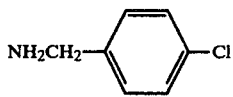

Recrystallization solvent
aq. Ethanol
melting point
193–195° C. (dec.)

Elemental analysis for $C_{16}H_{20}N_3SCl_3$

| | C | H | N |
|---|---|---|---|
| Calculated: | 48.93% | 5.13% | 10.70% |
| Found: | 48.72% | 5.11% | 10.50% |

EXAMPLE 28

Desired Compound

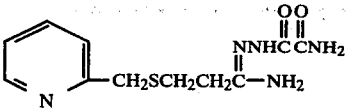

N—Oxamoyl-3-(2-pyridylmethylthio)-propionamidrazone
Reagent amine

Recrystallization solvent: Ethanol.
melting point: 149°–150° C.
Nuclear magnetic resonance spectra (DMSO-$d_6$). δ:
2.93 (4H, m), 3.86 (2H, s), 7.0~8.6 (4H).
Mass spectrum: m/e 281(M+), 263.

EXAMPLE 29

Desired Compound

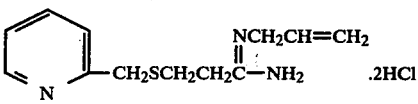

N—Allyl-3-(2-pyridylmethylthio)propionamidine
dihydrochloride
Reagent amine
$NH_2CH_2CH=CH_2$
Recrystallization solvent
Isopropanol
melting point
152–155° C. (dec.)

Elemental analysis for $C_{12}H_{19}N_3SCl_2$

| | C | H | N |
|---|---|---|---|
| Calculated: | 46.76% | 6.21% | 13.63% |
| Found: | 46.25% | 6.29% | 13.68% |

EXAMPLE 30

Desired Compound

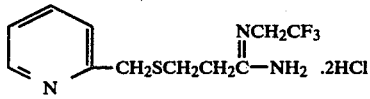

3-(2-Pyridylmethylthio-N—2,2,2-trifluoro-
ethylpropionamidine dihydrochloride
Reagent amine
$CF_3CH_2NH_2$
Recrystallization solvent
Ethanol-Ether
melting point
188–191° C.

Elemental analysis for $C_{11}H_{16}N_3SF_3Cl_2$

| | C | H | N |
|---|---|---|---|
| Calculated: | 37.72% | 4.60% | 12.00% |
| Found: | 37.76% | 4.74% | 11.96% |

EXAMPLE 31

Desired Compound

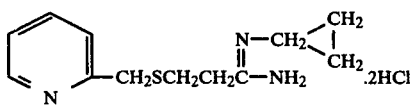

N—Cyclopropyl-3-(2-pyridylmethylthio)propion-
amidine dihydrochloride
Reagent amine

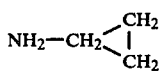

Recrystallization solvent
Ethanol-Ether
melting point
155–158° C.

Elemental analysis for $C_{12}H_{19}N_3SCl_2$

|  | C | H | N |
| --- | --- | --- | --- |
| Calculated: | 46.76% | 6.21% | 13.63% |
| Found: | 46.50% | 6.44% | 13.38% |

EXAMPLE 32

Desired Compound

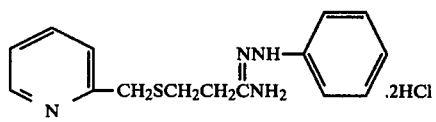

N—Phenyl-3-(2-pyridylmethylthio)propionamidrazone
dihydrochloride
Reagent amine

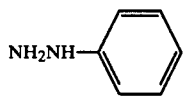

Recrystallization solvent
Ethanol-Ether
melting point
153–155° C. (dec.)

Elemental analysis for $C_{15}H_{20}N_4SCl_2 \cdot 3/2H_2O$

|  | C | H | N |
| --- | --- | --- | --- |
| Calculated: | 46.82% | 5.63% | 14.56% |
| Found: | 46.59% | 5.67% | 14.42% |

EXAMPLE 33

Desired Compound

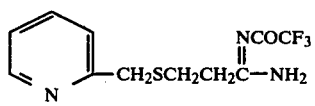

N—Trifluoroacetyl-3-(2-pyridylmethylthio)-
propionamidine
Reagent amine
$NH_2COCF_3$
Recrystallization solvent
Ethylacetate-Ether
melting point
113–116° C.

Elemental analysis for $C_{11}H_{12}N_3OSF_3 \cdot H_2O$

| Calculated: | 42.71% | 4.56% | 13.59% |
| --- | --- | --- | --- |
| Found: | 42.90% | 4.69% | 13.74% |

EXAMPLE 34

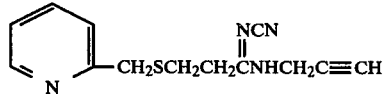

In 30 ml. of dry ether was dissolved 2.7 g. of ethyl N-cyano-3-(2-pyridylmethylthio)propionimidate and after adding 1.0 g. of proparglyamine to the solution followed by stirring for one hour at room temperature, the solvent was distilled off under reduced pressure. Then, the residue formed was purified by means of a silica gel column chromatography using a mixed solvent of methylene chloride and methanol as an eluant and recrystallized from a mixed solvent of ethyl acetate and n-hexane to provide 2.0 g. of the crystals of N-cyano-N'-(2-propynyl)-3-(2-pyridylmethylthio)propionamidine showing a melting point of 99°–100° C.

Elemental analysis for $C_{13}H_{14}N_4S$:

|  | C | H | N |
| --- | --- | --- | --- |
| Calculated: | 60.44% | 5.46% | 21.69% |
| Found: | 60.36% | 5.43% | 21.53% |

EXAMPLE 35

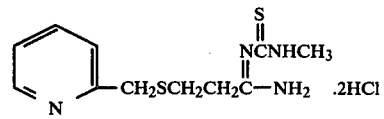

In 90 ml. of absolute methanol was dissolved 9.0 g. of 3-(2-pyridylmethylthio)-propionamidine dihydrochloride and after adding 50 ml. of a methanol solution of 3.6 g. of sodium methoxide to the solution under cooling below 10° C., the reaction mixture was allowed to rise to room temperature followed by stirring for one hour.

To the reaction mixture was added 50 ml. of a methanol solution of 2.4 g. of methyl isothiocyanate and after stirring the mixture for 5 hours at room temperature, the solvent was distilled off under reduced pressure. Then, the residue was purified by means of a silica gel column chromatography using a mixed solvent of chloroform and methanol as an eluant treated with hydrochloric acid, and then recrystallized from a mixed solvent of ethanol and ether to provide 1.1 g. of N-(N-methylthiocarbamoyl)-3-(2-pyridylmethylthio)propionamidine dihydrochloride.

Melting point: 147°–152° C. (decompd.)

Nuclear magnetic resonance spectra (d$_6$-DMSO): δ: 2.98 (3H, d, J=4 Hz, —NHCH$_3$); 3.09 (4H, s, —S—CH$_2$CH$_2$—); 4.39 (2H, s,

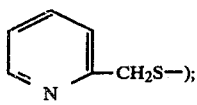

7.80~9.00 (4H,

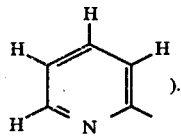

EXAMPLE 36

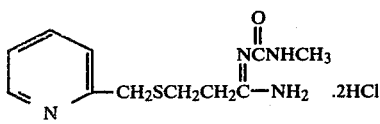

By following the same procedure as in Example 35 using methyl isocyanate in place of methyl isothiocyanate, 0.7 g. N-(N-methylcarbamoyl)-3-(2-pyridylmethylthio)propionamidine dihydrochloride was obtained from 11 g. of 3-(2-pyridylmethylthio)propionamidine dihydrochloride.

Melting point: 141°-146° C. (decompd.)

Nuclear magnetic resonance spectra (d$_6$-DMSO) δ: 2.70 (3H, d, J=4 Hz, —NHC$\underline{H}_3$); 3.02 (4H, s, —S—CH$_2$CH$_2$—); 4.34 (2H, s,

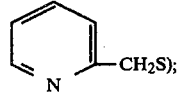

7.80~9.00 (4H,

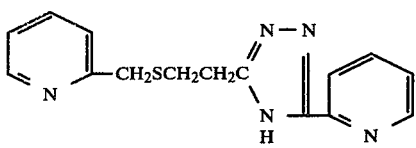

EXAMPLE 37

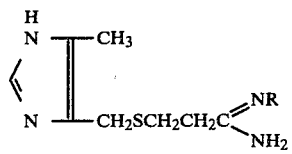

After heating 0.5 g. of N-picolinyl-3-(2-pyridylmethylthio)propionamidrazone to 130°-140° C. for 15 minutes, the residue formed was purified by means of a silica gel column chromatography using a mixed solvent of methylene chloride and methanol as an eluant and recrystallized from a mixed solvent of ethyl acetate and ether to provide 0.3 g. of 3-(2-pyridyl)-5-[2-(2-pyridylmethylthio)ethyl]-1,2,4-triazole showing a melting point of 98°-100° C.

Nuclear magnetic resonance spectra (CDCl$_3$). δ: 3.08 (4H, m, —S—CH$_2$CH$_2$—); 3.90 (2H, s, —CH$_2$S—); 7.0~8.80 (8H,

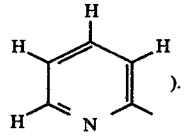

Mass spectrum: m/e 297(M+), 205.

EXAMPLE 38

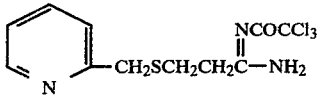

To 20 ml. of ice-cooled absolute ethanol solution of 2.0 g. of sodium methoxide was added 20 ml. of an absolute ethanol suspension of 5.0 g. of 3-(2-pyridylmethylthio)propionamidine dihydrochloride and after allowing to rise the mixture to room temperature followed by stirring for 1.5 hours, 3.6 g. of methyl trichloroacetate was added to the mixture. The resultant mixture was allowed to stand for 2 days at room temperature, the solvent was distilled off under reduced pressure, and the residue was purified by means of a silica gel column chromatography using a mixed solvent of methylene chloride and methanol and recrystallized from a mixture of ethanol and ether to provide 1.4 g. of N-trichloroacetyl-3-(2-pyridylmethylthio)propionamidine showing a melting point of 119°-120° C.

| Elemental analysis for C$_{11}$H$_{12}$N$_3$OSCl$_3$.H$_2$O: | | | |
|---|---|---|---|
| | C | H | N |
| Calculated: | 36.84% | 3.93% | 11.72% |
| Found: | 36.78% | 3.94% | 11.80% |

EXAMPLES 39-40

(a). In absolute ethanol was dissolved 12.2 g. of sodium in nitrogen gas stream and after cooling the solution to 0°-5° C., 50 ml. of an absolute ethanol solution of 23.1 g. of 3-mercaptopropionitrile was added to the solution followed by stirring for one hour. To the mixture was added 800 ml. of an absolute ethanol solution of 44.4 g. of 4-methyl-5-chloromethylimidazole hydrochloride and after stirring for 2 hours, the reaction mixture was allowed to rise to room temperature followed by further stirring for 18 hours. Then, NaCl deposited was filtered off, the solvent was distilled off under reduced pressure, and the residue was recrystallized from a mixture of ethanol and ether to provide 46.8 g. of 3-(4-methyl-5-imidazolylmethylthio)propionitrile.

(b). In 150 ml. of absolute ethanol was dissolved 10.0 g. of 3-(4-methyl-5-imidazolylmethylthio)propionitrile and after cooling the solution to 0°–5° C., 4.8 g. of a dry hydrogen chloride gas was absorbed in the solution. The solution was allowed to stand for one week at 0°–5° C. Then, the solvent was distilled off under reduced pressure and the crystals of ethyl 3-(4-methyl-5-imidazolylmethylthio)propionimidate dihydrochloride were washed with a mixed solvent of ethanol and ether and recovered by filtration. The amount of the product was 12.0 g.

(c). To an ice-cooled ethanol solution containing an equivalent of sodium ethoxide was added ethyl 3-(4-methyl-5-imidazolylmethylthio)propionimidate dihydrochloride followed by stirring for 15 minutes and after adding 1.5–5 equivalent of an amine ($RNH_2$), the mixture was allowed to stand for 24 hours at room temperature. The solvent was distilled off under reduced pressure and the residue was purified by means of a silica gel column chromatography using a mixed solvent of chloroform and methanol. If necessary, the product was treated with hydrochloric acid to form the hydrochloric of the product.

These are shown in the following table.

EXAMPLE 39

Desired Compound $$\begin{array}{c} H \\ N \end{array} \diagdown \!\!\! \diagup \!\!\! \begin{array}{c} CH_3 \\ \\ N \end{array} \!\!\! \diagdown \!\!\! \diagup \!\!\! \begin{array}{c} \\ CH_2SCH_2CH_2\overset{NCN}{\underset{\parallel}{C}}\!\!-\!\!NH_2 \end{array}$$

N—Cyano-3-[(5-methylimidazol-4-yl)methylthio]-propionamidine

Reagent amine: $NH_2CN$.
Recrystallization solvent: Isopropanol-Ethylacetate.
melting point: 147°–149° C.
Nuclear magnetic resonance spectra (DMSO-$d_6$). δ: 2.16 (3H,s), 2.70 (4H,s), 3.70 (2H,s), 7.44 (1H,s).

EXAMPLE 40

Desired Compound $$\begin{array}{c} H \\ N \end{array} \diagdown \!\!\! \diagup \!\!\! \begin{array}{c} CH_3 \\ \\ N \end{array} \!\!\! \diagdown \!\!\! \diagup \!\!\! \begin{array}{c} \\ CH_2SCH_2CH_2\overset{NCH_2C\equiv CH}{\underset{\parallel}{C}}\!\!-\!\!NH_2 \end{array} \quad .2HCl$$

N—2-Propynyl-3-[(5-methylimidazol-4-yl)methylthio]-propionamidine dihydrochloride (Caramel)

Reagent amine: $NH_2CH_2C\equiv CH$.
Nuclear magnetic resonance spectra (DMSO-$d_6$). δ: 2.20 (3H,s), 2.85 (4H,s), 3.44 (1H,t), 3.85 (2H,s), 4.21 (2H,d), 8.13 (1H,s).

EXAMPLES 41–42

$$\begin{array}{c} CH_3 \\ \\ CH_3 \end{array} \!\!\! \diagdown N\text{-}CH_2\text{-} \diagdown \!\!\! \diagup \!\!\! \begin{array}{c} \\ O \end{array} \!\!\! \diagdown \!\!\! \diagup \!\!\! \begin{array}{c} \\ \text{-}CH_2SCH_2CH_2\overset{NR}{\underset{\diagdown}{C}}\!\!\diagdown\!\! NH_2 \end{array}$$

(a) To 95 g. of furfurylmercaptan was added 0.2 g. of sodium methoxide and 53 g. of acrylonitrile was added gradually to the mixture with stirring while maintaining the reaction temperature at 40°–50° C. After stirring the mixture for 30 minutes at 40°–50° C., the reaction mixture was neutralized with 0.2 g. of acetic acid and distilled under reduced pressure to provide 135.5 g. of 3-(2-furanylmethylthio)-propionitrile showing a boiling point of 92°–93° C. (0.1 mm.Hg).

(b) In 600 ml. of absolute ethanol were dissolved 40 g. of 3-(2-furanylmethylthio)propionitrile, 39.0 g. of dimethylamine hydrochloride, and 16.7 g. of para-formaldehyde and the solution was refluxed for 24 hours. To the reaction mixture were added 39.0 g. of dimethylamine hydrochloride and 16.7 g. of para-formaldehyde and the mixture was further refluxed for 24 hours. Then, the solvent was distilled off under reduced pressure and the residue was mixed with 300 ml. of water. The mixture was alkalified by the addition of potassium carbonate and extracted three times each time with 200 ml. of ethyl acetate. The extract was dried over anhydrous potassium carbonate and the solvent was distilled off under reduced pressure. Then, the residue was distilled under reduced pressure to provide 41.6 g. of 3-(5-dimethylaminomethyl-2-furanylmethylthio)propionitrile showing a boiling point of 131°–137° C. (0.25 mm. Hg).

(c) In a mixture of 4.5 g. of absolute ethanol and 60 ml. of anhydrous chloroform was dissolved 19.8 g. of 5-dimethylaminoethyl-2-furanylmethylthio)propionitrile and after cooling the solution to 0°–5° C., 6.5 g. of a dry hydrogen chloride gas was added into the solution. After allowing to stand the reaction mixture in a refrigerator for one week, the mixture was added to 150 ml. of ice-water containing excess potassium carbonate and the product was extracted three times each time with 80 ml. of chloroform. The extract was dried over anhydrous potassium carbonate and then the solvent was distilled off under reduced pressure to provide 23 g. of ethyl 3-(5-dimethylaminomethyl-2-furanylmethylthio)propionimidate. The product was used in the subsequent reaction as it was.

(d) In absolute ethanol was dissolved ethyl 3-(5-dimethylaminomethyl-2-furanylmethylthio)propionimidate and after adding thereto a stoichiometric amount or a slightly excessive amount of an amine ($RNH_2$), the mixture was reacted for 24 hours at room temperature. Then, the solvent was distilled off under reduced pressure and, if necessary, the product was purified by means of a column chromatography to provide the objective product as shown in the following table.

EXAMPLE 41

Desired Compound $$\begin{array}{c} CH_3 \\ \\ CH_3 \end{array} \!\!\! \diagdown N\text{-}CH_2\text{-} \diagdown \!\!\! \diagup \!\!\! \begin{array}{c} \\ O \end{array} \!\!\! \diagdown \!\!\! \diagup \!\!\! \begin{array}{c} \\ \text{-}CH_2SCH_2CH_2\overset{NCN}{\underset{\parallel}{C}}\!\!-\!\!NH_2 \end{array}$$

N—Cyano-3-[5-(dimethylaminomethyl)furfurylthio]-propionamidine
Reagent amine
$NH_2CN$
Recrystallization solvent
Ethylacetate-Ether
melting point
70–72° C.
Nuclear magnetic resonance spectra (CDCl$_3$)
δ: 2.22 (6H,s), 2.40 (2H,m), 2.84 (2H,t),
3.38 (2H,s), 3.72 (2H,s), 6.12 (2H,s)

propionamidine showing a melting point of 169°–172.5° C.

| Elemental analysis for $C_9H_{17}N_5OSCl_2 \cdot \frac{1}{2}H_2O$: | | | |
|---|---|---|---|
| | C | H | N |
| Calculated: | 33.49% | 5.47% | 21.70% |
| Found: | 33.95% | 5.43% | 21.22% |

Nuclear magnetic resonance spectra (d$_6$-DMSO): δ: 2.32 (3H, s, —CH$_3$) 3.00 (4H, s, —S—CH$_2$—CH$_2$—) 4.04 (2H, s, —CH$_2$S—) 8.97 (1H, s,

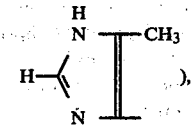
),

EXAMPLE 45

To 2-hydroxymethylpyridine was added 50 mg. of sodium methoxide and while maintaining the temperature of the reaction mixture at 50°–60° C. with stirring, 3.3 g. of acrylamide was added to the solution. The reaction mixture was stirred for 30 minutes at the same temperature, the crystals deposited were recrystallized from a mixed solution of ethanol and ether to provide 8.5 g. of the crystals of 3-(2-pyridylmethoxy)-propionamide showing a melting point of 94°–96° C.

| Elemental analysis for $C_9H_{12}N_2O_2$: | | | |
|---|---|---|---|
| | C | H | N |
| Calculated: | 59.99% | 6.71% | 15.55% |
| Found: | 59.80% | 6.67% | 15.45% |

EXAMPLE 46

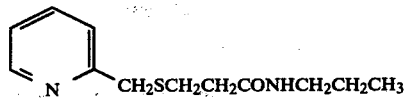

(a) In 100 ml. of 47% hydrobromic acid were dissolved 4.86 g. of 3-mercaptopropionic acid and 5 g. of 2-hydroxymethylpyridine and after refluxing the solution for 20 hours, the reaction mixture was concentrated under reduced pressure to provide 12.5 g. of sticky crude 3-(2-pyridylmethylthio)-propionic acid hydrobromide.

(b) To 4 g. of crude 3-(2-pyridylmethylthio)propionic acid hydrobromide was added 20 ml. dry chloroform and after cooling the mixture to 0°–5° C., 3.5 g. of triethylamine was added to the mixture followed by stirring for 30 minutes. Thereafter, a solution of 1.56 g. of ethyl chlorocarbonate in 5 ml. of dry chloroform was added to the mixture followed by stirring for one hour.

Then, to the reaction mixture was added a solution of 1.3 g. of n-propylamine in 5 ml. of dry chloroform and

---

-continued

| Infrared absorption spectrum (KBr tab) cm$^{-1}$: 2180 | | | |
|---|---|---|---|
| Elemental analysis for $C_{12}H_{18}N_4OS$ | | | |
| | C | H | N |
| Calculated: | 54.11% | 6.81% | 21.03% |
| Found: | 54.15% | 6.85% | 21.22% |

EXAMPLE 42

Desired Compound

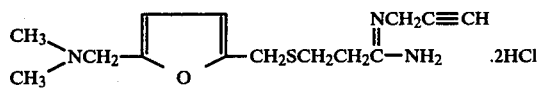

3-[5-(Dimethylaminomethyl)furfurylthio]-N—
2-propynylpropionamidine dihydrochloride
Reagent amine
NH$_2$CH$_2$C≡CH
Recrystallization solvent
Ethanol-Ether
melting point
176–178° C.
Nuclear magnetic resonance spectra (DMSO-d$_6$)
δ: 2.68 (6H,s), 2.88 (4H,s), 3.44 (1H,t), 3.94 (2H,s)
4.22 (2H,d), 4.36 (2H,s), 6.50 (1H,d), 3.70 (1H,d)

| Elemental analysis for $C_{14}H_{23}N_3OSCl_2$ | | | |
|---|---|---|---|
| | C | H | N |
| Calculated: | 47.73% | 6.58% | 11.93% |
| Found: | 47.44% | 6.91% | 11.80% |

EXAMPLE 43

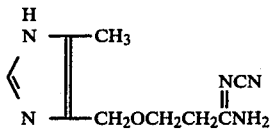

By following the same procedure as in Example 1-(a), 3-(4-methyl-5-imidazolylmethoxy)propionitrile was obtained from 4-hydroxylmethyl-5-methyl-imidazole and acrylonitrile and by treating the product as in Example 1-(b), ethyl 3-(4-methyl-5-imidazolylmethoxy)propionimidate was obtained. Then, by further treating the product as in Example 1-(c), N-cyano-3-(4-methyl-5-imidazolylmethoxy)propionamidine was obtained.

Infrared absorption spectrum (cm.$^{-1}$): 2160.
Mass spectrum (m/c): 207 (M+).

EXAMPLE 44

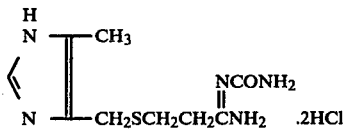

In 30 ml. of absolute ethanol was dissolved 1.0 g. of N-cyano-3-(4-methyl-5-imidazolylmethylthio)propionamidine and after cooling the solution to 0°–5° C., a dry hydrogen chloride gas was passed through the solution slowly for one hour. Then, the solvent was concentrated under reduced pressure and the crystals deposited were recovered by filtration to provide 1.0 g. of N-carbamoyl-3-(4-methyl-5-imidazolylmethylthio)- after allowing to rasie the mixture to room temperature followed by stirring for 3 hours, 20 ml. of chloroform was added to the mixture. The chloroform layer was washed with water, dried over anhydrous magnesium sulfate, and concentrated under reduced pressure. The residue was purified by means of a silica gel column chromatography using a mixed solvent of methylene chloride and ethyl acetate as an eluant to provide 1.2 g. of oily N-propyl-3-(2-pyridylmethylthio)propionamide.

Infrared absorption spectrum (cm$^{-1}$): 1640.

Nuclear magnetic resonance spectra (CDCl$_3$): δ: 0.88 (3H, t, J=7 Hz, NHCH$_2$CH$_2$CH$_3$), 1.49 (2H, m, NHCH$_2$CH$_2$CH$_3$), 2.44 (2H, t, J=7 Hz, CH$_2$SCH$_2$CH$_2$CO), 2.76 (2H, t, J=7 Hz, CH$_2$SCH$_2$CH$_2$CO), 3.17 (2H, q, NHCH$_2$CH$_2$CH$_3$), 3.83 (2H, s, CH$_2$SCH$_2$—).

Mass Spectrum: m/e 238(M+), 180.

EXAMPLE 47

(a) In 50 ml. of dry tetrahydrofuran was suspended 7.5 g. of 50% sodium hydride in oil in nitrogen gas stream and after adding gradually 16.6 g. of 2-mercaptoacetic acid methyl ester with stirring, they were reacted for 30 minutes at room temperature. Then, a solution of 20 g. of 2-chloromethylpyridine in 20 ml. of dry tetrahydrofuran was added to the mixture below room temperature and stirring for 20 hours. After distilling off the solvent under reduced pressure, the residue formed was mixed with 70 ml. of water and extracted three times each time with 100 ml. of ether. The ether layer was washed with water, dried over anhydrous magnesium sulfate, concentrated under reduced pressure, and distilled under reduced pressure to provide 28.3 g. of 2-pyridylmethylthio acetic acid methyl ester showing a boiling point of 110°–114° C. (0.9 mm.Hg).

(b) In 40 ml. of a 40% methanol solution of methylamine was dissolved 5 g. of 2-pyridylmethylthioacetic acid methyl ester and after allowing to stand the solution for 20 hours at room temperature, the reaction mixture was concentrated under reduced pressure and the residue was purified by means of a silica gel column chromatography using a mixed solvent of methylene chloride and ethyl acetate as an eluant to provide 1.7 g. of oily N-methyl-2-(2-pyridylmethylthio)-acetamide.

Nuclear magnetic resonance spectra (CDCl$_3$): δ: 2.78 (3H, d, J=5 Hz, NHCH$_3$), 3.17 (2H, s, CH$_2$SCH$_2$CO), 3.85 (2H, s, CH$_2$SCH$_2$CO).

Mass Spectrum: m/e 196(M+), 138, 124.

EXAMPLE 48

In 5 ml. of dry methanol was dissolved 3 g. of 3-(2-pyridylmethylthio)-propionic acid methyl ester prepared according to Example 47-(a) and after adding thereto a solution of 78.0 mg. of free guanidine in 15 ml. of dry methanol, the mixture was allowed to stand for 24 hours. The crystals thus deposited were recrystallized twice each time with a mixture of ethanol and ether to provide 0.8 g. of N-3-(2-pyridylmethylthio)propionylguanidine showing a melting point of 149°–150.5° C.

Infrared absorption spectrum (cm$^{-1}$): 1660.

Nuclear magnetic resonance spectra (d$_6$-DMSO): δ: 2.19 (2H, t, J=7 Hz, CH$_2$CH$_2$CO), 2.64 (2H, t, J=7 Hz, —SCH$_2$CH$_2$CO), 3.80 (2H, s, CH$_2$SCH$_2$CH$_2$CO).

EXAMPLE 49

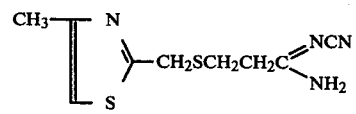

(a) To an ethanol solution of sodium ethoxide (i.e., a solution prepared by dissolving 1.6 g. of metallic sodium in 100 ml. of ethanol) was added dropwise under ice-cooling a solution of 10 g. of 2-chloromethyl-4-methylthiazole in 30 ml. of ethanol and the mixture was stirred overnight at room temperature. Then, ethanol was distilled off from the reaction mixture under reduced pressure and the residue was extracted three times each time with 100 ml. of ether. The ether extract was dried over anhydrous potassium carbonate and the solvent was distilled off under reduced pressure to provide 12 g. of oily 3-{(4-methylthiazol-2-yl)methylthio}-propionitrile.

Mass spectrum: m/e 198.

(b) In a mixture of 36 ml. of chloroform and 4.2 ml. of ethanol was dissolved 12 g. of 3-{(4-methylthiazol-2-yl)methylthio}propionitrile and after passing 7 g. of a hydrogen chloride gas through the solution under ice-cooling, the reaction mixture was maintained at 0°–5° C. for 8 days. The reaction mixture was poured in ice-water containing 50 g. of potassium carbonate and extracted three times each time with 100 ml. of chloroform. The chloroform extract was dried over anhydrous potassium carbonate and then the solvent was distilled off under reduced pressure to provide 14.5 g. of oily ethyl 3-{(4-methylthiazol-2-yl)methylthio}propionimidate.

(c) In 60 ml. of ethanol were dissolved 10 g. of ethyl 3-{(4-methylthiazol-2-yl)methylthio}propionimidate and 1.9 g. of cyanamide and the solution was allowed to stand overnight at room temperature. The reaction mixture was concentrated under reduced pressure and the residue was washed with ethyl acetate to provide 7.7 g. of N-cyano-3-{(4-methylthiazol-2-yl)-methylthio}propionamide showing a melting point of 114°–115° C.

| Elemental analysis for C$_9$H$_{12}$N$_4$S$_2$: | | |
|---|---|---|
| C | H | N |
| Calculated: 44.98% | 5.03% | 23.31% |
| Found: 45.08% | 4.96% | 23.37% |

EXAMPLE 50

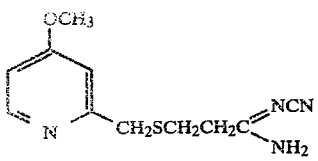

(a) In 100 ml. of an ethanol solution of sodium ethoxide (i.e., a solution prepared by dissolving 2.6 g. of metallic sodium in 100 ml. of ethanol) and after adding to the solution 11 g. of 2-chloromethyl-4-methoxypyridine hydrochloride under cooling with ice-water, the mixture was stirred overnight at room temperature. The reaction mixture was concentrated under reduced pressure and the residue was mixed with 100 ml. of water and extracted three times each time with 100 ml. of ether. The ether extract was dried over anhydrous potassium carbonate and then the solvent was distilled off under reduced pressure to provide 10.5 g. of oily 3-{(4-methoxypyridine-2-yl)methylthio}propionitrile.

(b) In a mixture of 30 ml. of chloroform and 3.5 ml. of ethanol was dissolved 10.5 g. of 3-{(4-methoxypyridine-2-yl)methylthio}propionitrile and after passing 6 g. of a hydrogen chloride gas through the solution under cooling with ice-water, the solution was allowed to stand for 8 days at 0°–5° C. The reaction mixture was poured in ice-water containing 50 g. of potassium carbonate and extracted three times each time with 100 ml. of chloroform. The chloroform extract was dried over anhydrous potassium carbonate and then the solvent was distilled off under reduced pressure to provide 12 g. of oily ethyl 3-(4-methoxypyridine-2-yl)methylthio propionimidate.

(c) In 70 ml. of ethanol were dissolved 12 g. of ethyl 3-{(4-methoxypyridine-2-yl)methylthio}propionimidate and 2.2 g. of cyanamide and the solution was allowed to stand overnight. The reaction mixture was concentrated under reduced pressure and the residue was purified by means of a silica gel column chromatography using a mixed solvent of chloroform and ethanol as an eluant to provide 11.5 g. of the crystals of N-cyano-3{(4-methoxypyridine-2-yl)methylthio}propionamidine showing a melting point of 132°–133° C.

| Elemental analysis for $C_{11}H_{14}N_4OS$: | | | |
|---|---|---|---|
| | C | H | N |
| Calculated: | 52.78% | 5.64% | 22.38% |
| Found: | 52.59% | 5.58% | 22.46% |

EXAMPLE 51

Medical composition: Tablets for oral administration.
Composition for 1,000 tablets:

| | |
|---|---|
| N—Carbamoyl-3-(4-methyl-5-imidazolyl-methylthio)propionamidine | 200 g. |
| Starch | 37 g. |
| Milk sugar | 50 g. |
| Magnesium stearate | 3 g. |

The above components were granulated using a starch paste as a binder and shaped into tablets of 9.5 mm. diameter by a conventional manner.

EXAMPLE 52

Medical composition: Formulation for injection.
Composition in 2 ml. of injection:

| | |
|---|---|
| N—Carbamoyl-3-(4-methyl-5-imidazolyl-methylthio)propionamidine.2HCl | 260 mg. |
| Distilled water for injection (the Japan Pharmacopoeia) to make 2 ml. | |

The active component was dissolved in distilled water for injection while passing therethrough a nitrogen gas and the solution was adjusted to a concentration of 13% (a concentration of 10% as base). The solution was filtered by a bacterial filter and 2.2 ml. of the solution was poured in each 2 milliliter ampule in a sterilized state. Then, after replacing the space of the ampule with nitrogen gas, the ampule was sealed.

EXAMPLES 53–59

By following the same procedure as described in Examples 41–42, except for differing starting materials, the following products were obtained.

EXAMPLE 53

Desired compound

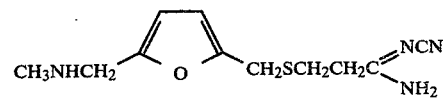

N—Cyano-3-[5-(methylaminomethyl)furfurylthio]propionamidine

Reagent amine: $H_2NCN$.
Melting point: 75°–83° C.
Recrystallization solvent: Ethanol-Ether.
Nuclear magnetic resonance spectra (DMSO-$d_6$): δ: 2.28 (3H, s, NH$CH_3$), 2.5–2.9 (4H, m, —$CH_2CH_2$—), 3.64 (2H, s, —$CH_2$—N<), 3.80 (2H, s,

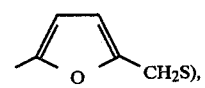

6.1–6.3 (2H, m,

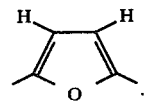

Infrared absorption spectrum (KBr tab) cm$^{-1}$: 2160.

EXAMPLE 54

Desired compound

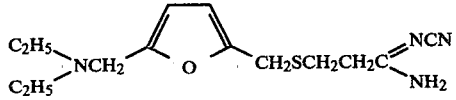

N—cyano-3-[5(diethylaminomethyl)furfurylthio]propionamidine

Reagent amine: $H_2NCN$.

Nuclear magnetic resonance spectra (CDCl₃): δ: 1.08 (6H, t, —CH₂C$\underline{H_3}$), 2.5–2.9 (8H, m, —C$\underline{H_2}$CH₃, —SC$\underline{H_2}$C$\underline{H_2}$—), 3.58 (2H, s, —C$\underline{H_2}$N<), 3.80 (2H, s,

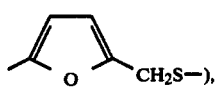

), 6.20 (2H, s,

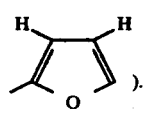

).

Infrared absorption spectrum (neat cm⁻¹: 2160.

EXAMPLE 55

| Desired compound |
| --- |
| 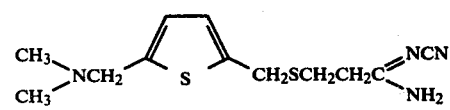 |

N—Cyano-3-[5-(dimethylaminomethyl)thienylmethylthio]propionamidine
Reagent amine
H₂NCN
Melting point
135–136° C.

| Elemental analysis for C₁₂H₁₈N₄S₂ | | |
| --- | --- | --- |
| C (%) | H (%) | N (%) |
| Calculated: 51.03 | 6.42 | 19.84 |
| Found: 50.77 | 6.49 | 19.89 |

EXAMPLE 56

Desired compound

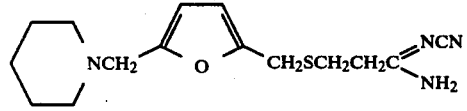

N—cyano-3-[5-(piperidinomethyl)furfurylthio]propionamidine

Reagent amine: H₂NCN.
Melting point: 102°–103° C.
Recrystallization solvent: Ethyl acetate.

| Nuclear magnetic resonance spectra (DMSO-d₆) |
| --- |
| δ: |
| 1.2–1.6(6H, m, 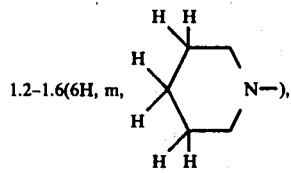), |
| 2.1–2.5(4H, m, 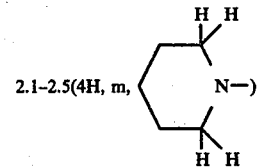) |
| 2.5–2.8(4H, m, —S—CH₂CH₂—), |
| 3.38(2H, s, 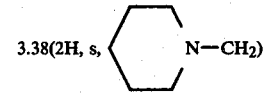) |
| 3.78(2H, s, 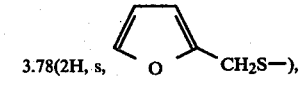), |
| 6.1–6.3(2H, m, 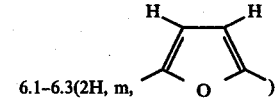) |

Infrared absorption spectrum (KBr tab) cm⁻¹: 2160.

EXAMPLE 57

Desired compound

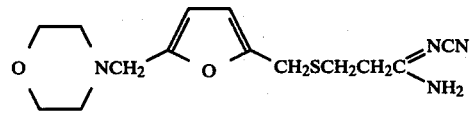

N—Cyano-3-[5-(morpholinomethyl)furfurylthio]propionamidine

Reagent amine: H₂NCN.

| Nuclear magnetic resonance spectra (CDCl₃) |
| --- |
| δ: |
| 2.4–2.9(8H, m, 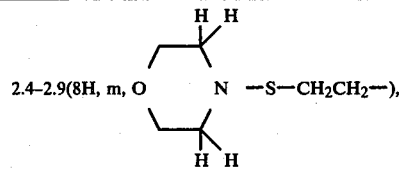 —S—CH₂CH₂—), |
| 3.48(2H, s, 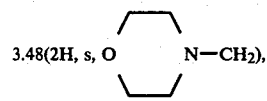), |
| 3.60–3.61(4H, m, 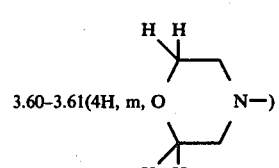) |
| 3.73(2H, s, 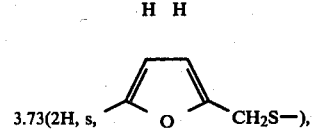), |

-continued

Nuclear magnetic resonance spectra (CDCl₃)

6.14(2H, s, 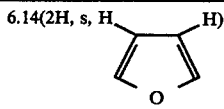)

Infrared absorption spectrum (neat) cm⁻¹: 2160.

EXAMPLE 58

Desired compound

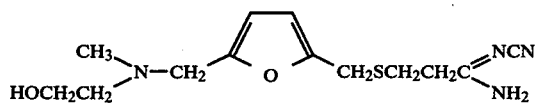

N—Cyano-3-[5-N—(2-hydroxyethyl)-N—methylaminomethylfur-furylthio]-propionamidine
Reagent amine
H₂NCN
Nuclear magnetic resonance spectra (CDCl₃)

δ:
2.28(3H, s, 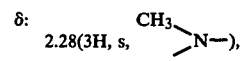), 2.4–2.9(6H, m, S—CH₂CH₂—, 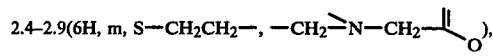), 3.56(2H, s, 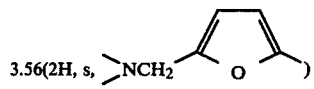)

3.6–3.8(2H, m, HOCH₂CH₂ 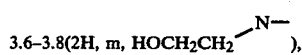), 3.76(2H, s, 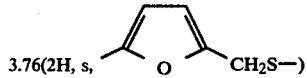)

6.18(2H, s, 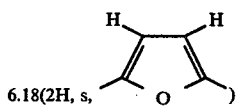)

Infrared absorption spectrum (neat) cm⁻¹: 2160

EXAMPLE 59

Desired compound

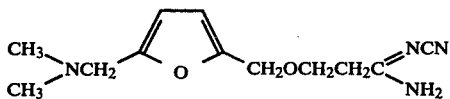

N—Cyano-3-[5-(dimethylaminomethyl)furfuryloxy]propionamidine
Reagent amine
H₂NCN
Nuclear magnetic resonance spectra (CDCl₃)

δ:
2.22(6H, s, 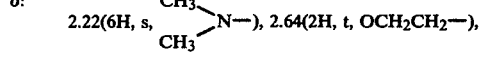), 2.64(2H, t, OCH₂CH₂—), 3.41(2H, s, 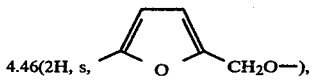), 3.74(2H, t, —OCH₂CH₂), 4.46(2H, s, 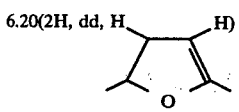), 6.20(2H, dd, 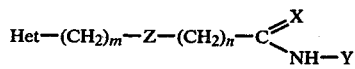)

Infrared absorption spectrum (neat) cm⁻¹: 2160

What is claimed is:

1. A heterocyclic compound of the formula $$Het-(CH_2)_m-Z-(CH_2)_n-C\underset{NH-Y}{\overset{X}{\lessgtr}}$$

wherein Het represents imidazolyl, either unsubstituted or substituted by halogen, hydroxyl, lower alkyl, lower alkoxy, hydroxymethyl, phenyl, benzyl, cyano, amino, aminoalkyl, amidinoalkyl; Z represents sulfur or oxygen; X represents the formula N—R₁ wherein R₁ represents cyano, unsubstituted or lower alkyl-substituted carbamoyl, unsubstituted or lower-alkyl-substituted thiocarbamoyl; Y represents alkyl substituted by hydroxyl, amino or halogen, cycloalkyl of 3–6 carbon atoms, lower alkenyl, lower alkynyl, aryl, unsubstituted or substituted by hydroxyl, amino or halogen, aralkyl, unsubstituted or substituted by hydroxyl, amino, or halogen, cyano, or carbamoyl; and m and n represent an integer of 1 to 3; or a pharmacologically acceptable acid addition salt thereof.

2. A compound according to claim 1, which is N-2-propynyl-3-[(5-methylimidazol-4-yl)methylthio]-propionamidine and the dihydrochloride salt thereof.

3. A compound according to claim 1, which is N-carbamoyl-3-(4-methyl-5-imidazolylmethylthio)-propionamidine.

4. A composition for inhibiting gastric acid secretion containing as the active ingredient an effective amount of a heterocyclic compound of claim 1 and a pharmaceutically acceptable carrier.

5. The composition according to claim 4, wherein the active ingredient is N-2-propynyl-3-[(5-methylimidazol-4-yl)methylthio]-propionamidine or the dihydrochloride salt thereof.

6. The composition according to claim 4, wherein the active ingredient is N-carbamoyl-3-(4-methyl-5-imidazolyl-methylthio)-propionamidine.

7. A composition for oral administration as claimed in claim 4, containing a sufficient amount of said compound to provide a dose of from 0.4 to 1 g per day when administered in 1 to 4 divided doses per day.

8. A method of inhibiting gastric acid secretion in a warm blooded animal which comprises administering an effective amount of the composition of claim 4 to said warm blooded animal.

9. The method as claimed in claim 8 wherein said composition is administered orally in an amount varying from 0.4 to 1 g each day.

* * * * *